(12) United States Patent
Colman et al.

(10) Patent No.: US 8,992,430 B2
(45) Date of Patent: Mar. 31, 2015

(54) BREATH SAMPLING SYSTEM

(75) Inventors: Joshua Lewis Colman, Jerusalem (IL); Gershon Levitsky, Jerusalem (IL)

(73) Assignee: Oridion Medical 1987 Ltd., Jerusalem (IL)

( * ) Notice: Subject to any disclaimer, the term of this patent is extended or adjusted under 35 U.S.C. 154(b) by 1020 days.

(21) Appl. No.: 12/739,900

(22) PCT Filed: Oct. 25, 2007

(86) PCT No.: PCT/IL2007/001294
§ 371 (c)(1),
(2), (4) Date: Aug. 6, 2010

(87) PCT Pub. No.: WO2009/053958
PCT Pub. Date: Apr. 30, 2009

(65) Prior Publication Data
US 2010/0298734 A1 Nov. 25, 2010

(51) Int. Cl.
*A61B 5/02* (2006.01)
*A61B 5/087* (2006.01)
*A61B 5/083* (2006.01)

(52) U.S. Cl.
CPC ............... *A61B 5/087* (2013.01); *A61B 5/083* (2013.01)
USPC ..................................................... 600/481

(58) Field of Classification Search
CPC .............................. A61B 5/083; A61B 5/087
USPC ................................................. 600/543, 532
See application file for complete search history.

(56) References Cited

U.S. PATENT DOCUMENTS

| | | | |
|---|---|---|---|
| 4,476,708 A | | 10/1984 | Baker et al. |
| 4,592,368 A | * | 6/1986 | Ricciardelli et al. ........... 600/532 |
| 4,799,374 A | * | 1/1989 | Bossart et al. ................. 250/343 |
| 4,924,860 A | | 5/1990 | Larsen et al. |
| 5,129,401 A | * | 7/1992 | Corenman et al. ............. 600/529 |
| 5,394,881 A | | 3/1995 | Block, Jr. |
| 5,451,373 A | * | 9/1995 | Lewis et al. ................. 422/82.13 |
| 5,857,461 A | * | 1/1999 | Levitsky et al. .......... 128/207.14 |
| 2006/0086254 A1 | * | 4/2006 | Fudge et al. ..................... 96/413 |

* cited by examiner

*Primary Examiner* — Michael D'Angelo
*Assistant Examiner* — Christian Jang
(74) *Attorney, Agent, or Firm* — Browdy and Neimark, PLLC (57) ABSTRACT

There is provided herein a breath sampling device comprising a controller adapted to initiate a signal to trigger a valve functionally associated with a breath sampling tube upon said controller receiving a signal indicating a blockage in the breath sampling tube. The valve is adapted to facilitate an increase of pressure within the breath sampling tube between the blockage and a pump functionally associated with the breath sampling tube. There is further provided herein an airway adapter comprising a restrictor located in proximity to a connection point between the airway adapter and a breath sampling tube, wherein the restrictor may be adapted to reduce the flow rate of liquids entering the breath sampling tube. There is further provided herein an airway adapter comprising one or more openings located near a connection point between said airway adapter and a breath sampling tube, wherein said one or more openings are adapted to allow inflow of air to reduce the flow rate of liquids entering the breath sampling tube.

7 Claims, 8 Drawing Sheets

BREATH SAMPLING SYSTEM

FIELD OF THE DISCLOSURE

The invention relates to breath sampling devices.

BACKGROUND

In Capnography, monitoring of the concentration of exhaled carbon dioxide is generally performed to assess the physiological status of patients with respiratory problems, including those receiving mechanical ventilation, and to determine the adequacy of ventilation in anaesthetized patients. Two methods are typically employed, Mainstream Capnography and Side-stream Capnography.

In a mainstream Capnography system, a breath measuring device is directly coupled, through an appropriate adapter, to a patient airway tube connecting the patient to a ventilation machine. A sensor is fitted onto the airway tube so that the exhaled breath is detected by the sensor which measures the carbon dioxide concentration in the exhaled breath. The method is generally used with intubated patients as, for non-intubated patients, a mask is usually required which may be uncomfortable for patients in respiratory distress.

In a side-stream Capnography system, a breath sampling device continuously draws samples of exhaled breath from the attached patient airway tube connecting the patient to the ventilation machine. The accuracy in the measurement and analysis of the samples of breath is dependent on a continuous, smooth, laminar flow in the exhaled gases when traveling from the patient to the breath sampling device, such that the effect on the exhaled gas waveform is maintained to a minimum. Hereinafter, the use of the term "minimum effect on the waveform of the exhaled breath sample" or "effect on the exhaled gas waveform is maintained to a minimum" shall be understood to mean that the effect on the waveform will be such that the accuracy of the measurements by the breath sampling device will not be affected. Typical of this method, the breath samples are generally transferred via an airway adapter positioned in the patient airway tube and which includes one or a plurality of breath sampling ports, through a narrow diameter flexible tube, referred to as a breath sampling tube, towards the measuring sensor. A liquid filtering system is used for controlling and handling liquids generally encountered in a medical environment which commonly accumulate in the patient airway tube and enter the breath sampling tube. Some examples of these liquids may be related to patient secretions, condensed-out liquids resulting from high humidity in the ventilation means, and medications and saline solutions provided to a patient during lavage, suction and nebulization procedures.

In a typical side-stream Capnography system, the airway adapter may comprise a tube of approximately 15 mm internal diameter and some 60 mm long, and includes appropriate fittings at either end, serially connected to the patient airway tubing. Midway along the tube may be attached the sampling port, which may be also a plurality of sampling ports, the sampling port comprising a small bore tube, typically 1 mm-2 mm internal diameter, and including one or more inlets. The sampling port is generally positioned perpendicular to the axis of exhaled gas flow in the patient airway tubing, reaching close to the center of the airway adapter tube at one end and exiting the airway adapter tube for connection to one end of the breath sampling tube at the other end. At the other end of the breath sampling tube is connected the breath sampling device, which includes a pump, which may be, for example, a diaphragm pump, which continuously creates a pressure drop at the inlet of the sampling port with respect to the airway adapter. This enables a continuous sample of breath to enter the sampling port and flow through the breath sampling tube to the measurement sensor for analysis (except when blockages occur, as explained below).

The liquid filtering systems are generally designed with three parameters in mind. First, minimize any effect on the waveform of the breath samples to maintain accurate measurements. Second, minimize the possibility of liquids collecting in the breath sampling tube to avoid interference with the monitoring of continuous samples of breath by the breath sampling device. Third, restrict liquids from reaching the sensitive components of the breath sampling device to avoid possible damage to the device. Numerous methods are available which address these parameters; some are based on preventing liquids from entering the breath sampling tube and others are based on removing the liquids once inside the breath sampling tube. The following are a few examples:

a. A specially designed airway adapter fitted on the patient airway tubing to which is connected the breath sampling tube.

b. A Nation (or similar) tube, which may form part of the breath sampling tube, for reducing humidity and consequently reducing the possibility of condensed-out liquids collecting.

c. A reservoir or other liquid collection means in the breath sampling tube adapted to collect liquids flowing into the breath sampling tube, such that the exhaled gas sample may continue to flow undisturbed towards the measurement sensor.

d. A hydrophobic fuse, also referred to as a hydrophobic block or filter, located before the breath sampling device to trap any liquids which have managed to pass the other elements of the filtering system and to prevent them from entering into the device.

e. A measurement sensor, which includes software that is able to detect an inflow of liquid into the breath sampling tube, generally based on sensing an increase in the pressure drop in the breath sampling tube. The sensor may be programmed to react by drawing the liquid into a reservoir or other type of liquid collection element in the filtering system, or to stop the sampling, possibly shutting down the sensor altogether.

Situations may periodically arise wherein relatively large quantities of liquid enter into the breath sampling tube through the sampling port(s) as a consequence of the sampling port(s) being temporarily submerged in liquid. This may occur, for example, when the airway tubing and/or the patient are periodically moved and liquid collecting within the airway tubing splashes from one side to the other, or during lavage when a saline solution is injected into the airway tubing towards the patient's lungs to break down secretions. Another possible occurrence may be when the airway adapter is the lowest point in the airway tubing so that liquids from condensed-out humidity, secretions, medications and other sources collect at the bottom of the airway adapter and splash into the sampling port(s).

When the sampling port is temporarily submerged in liquid, blockage of the sampling port may occur. A blockage refers to a partial or complete obstruction in the flow path of the breath samples due to liquids. This may result in an increase in the negative pressure in the breath sampling tube due to the suctioning action of the pump in the breath sampling device. As the negative pressure continues to increase, a vacuum is created, the vacuum level dependent on the pump strength and the location of the blockage relative to the length of the breath sampling tube. The increased pressure differential between the higher pressure in the airway adapter and the vacuum in the breath sampling tube induces a greater quantity of liquid to flow into the sampling port and into the breath sampling tube. Furthermore, even if the sampling ports have been cleared from any liquid, the liquid accumulated in the breath sampling tube is pulled towards the breath sampling device as the negative pressure further increases due to the pump's suctioning action, the increase a function of the distance the liquid is from the pump.

Breath sampling devices used in Capnography generally include a pressure sensor adapted to measure absolute pressure in the breath sampling tube, necessary for the device to be able to correct for $CO_2$ concentrations as a function of the gas sampled pressure. Typically, commercially available Capnographs are adapted to use the pressure sensor to also monitor blockage conditions such that, when the pressure drop in the breath sampling tube reaches a predetermined threshold, for example, a predetermined value between 60 mbars to 150 mbars, a controller in the Capnograph will interpret this condition to be a blockage condition in the breath sampling tube.

Generally, the controller in the breath sampling device will respond to a blockage by instructing the pump to either increase pumping rate, to continue to pump at the same rate, or to turn off the pump. In each of the first two cases the negative pressure in the breath sampling tube is further increased in the segment between the blockage and the device. This corrective action is taken in an attempt to draw the trapped liquid into one of the liquid collection elements, as previously described, in which case the blockage will be removed. Following a period of pump operation is a time-out period, during which the pump ceases to operate and the controller checks to see if the blockage has been cleared. This is generally done by checking that the pressure sensor is monitoring a second threshold pressure drop where the negative pressure in the breath sampling tube is less than the first threshold. If the negative pressure is less than or equal to the second threshold, then the controller interprets this as the blockage having been removed and the breath sampling device may return to normal operation.

There are numerous drawbacks in the methods previously described for limiting and removing blockages in the breath sampling tube when relatively large quantities of liquid enter into the sampling ports and the breath sampling tube. These are described below:

a. There is a supposition that only a small amount of liquid will enter the sampling port and the breath sampling tube on each occurrence, less than the volume capacity of the liquid collection element, and that the sampling port will be submerged in the liquid for only a relatively short period of time. Nevertheless, this is not always the case, and periodically there may be situations in which relatively large quantities of liquid are sucked into the sampling port and into the breath sampling tube, and then drawn along part or the whole length of the breath sampling tube by the increasing negative pressure resulting from the suctioning pull of the pump in the breath sampling device.

b. Design parameters for the liquid collection elements in the liquid filtering system require that the effect on the sampled breath waveform be maintained to a minimum so as to not affect the accuracy of the measurements. Generally, this imposes a series of constraints on the design of the elements, limited by the complex design of the interface between the liquid collection element and the gas flowing portion of the breath sampling tube. The result is that the collection rate of the liquid collection elements is limited to relatively lower rates and, when large quantities of liquid are involved, the liquid often bypasses the liquid collection elements continuing downstream via the breath sampling tube to reach the hydrophobic fuse. There the liquids may block the system, or may even find their way into the device, possibly damaging components in the device.

c. Generally the most effective liquid collection elements that cause the least effect on the sampled breath waveform have limited volumes for collection, typically only a few hundred micro liters. This volume contrasts sharply with that of the breath sampling tube which generally has a volume exceeding 2 cc, such that the protection offered by the liquid collection element is limited compared to the capacity of liquid which may be held by the breath sampling tube. As previously mentioned, a large quantity of liquid periodically enters into the breath sampling tube so that, if the liquid collection element is limited in volume, not all the liquid will be retained by the liquid collection elements. This may result in blockage in the breath sampling tube or the liquid continuing downstream via the breath sampling tube to reach the hydrophobic fuse, where it may either block the system or may even find its way into the device, possibly causing damage.

d. In those cases where only a filter serves as the liquid collection means (element), due to the very small volume of the filter, it quickly fills up so that all the liquid may not be collected and removed from interfering with the breath sampling. This may result in blockage in the breath sampling tube or the liquid continuing downstream via the breath sampling tube to reach the hydrophobic fuse, where it may either block the system or may even find its way into the device, possibly causing damage.

As discussed above breath sampling systems known in the art are not readily adapted to handle exposure to relatively large amounts of liquids periodically encountered in applications related to side-stream Capnography. These breath sampling systems have a tendency to suffer from blockages, due to the inability of their liquid filtering system to collect the amounts of liquid which periodically flow into the breath sampling tube and which may exceed the volumetric capacity of the liquid collecting elements in the liquid filtering system. Test results show that more than 1 cc of liquid can flow into the breath sampling tube, causing the tube to block. The high frequency of blockages results in the breath sampling system requiring constant supervision and maintenance, and repeated replacement of the breath sampling tube. There is, therefore, a need for a breath sampling system capable of handling exposure to relatively large amounts of liquid which may be periodically encountered in applications related to side-stream Capnography.

The terms "blockage" or "block" may refer to any type of resistance to undisturbed gas flow in any part of a tube, such as a sampling tube. The blockage may be a partial blockage which allows some gas flow in the tube, or a complete blockage which entirely blocks gas flow.

SUMMARY

An aspect of some embodiments of the invention relates to providing a method and device for reducing the occurrences of blockages in a breath sampling tube, and optionally, for clearing the blockages if and when they occur.

According to some embodiments, of the invention a lower pressure in a section of the sampling tube on one side of a blockage may be substantially equalized with a higher pressure in a second section of the breath sampling tube on a second side of the blockage. Both pressures may be substantially equalized by enabling the flow of air, or optionally another gas, into the lower pressure section of the breath sampling tube. Substantially equalizing the pressure on both sides of the blockage restricts liquids from further being drawn into the breath sampling tube, allowing the blockage to diffuse and the liquids to flow into liquid collection means.

In an embodiment of the invention, there is provided a breath sampling device comprising a fast response pressure sensor, a controller and a valve. The breath sampling device is adapted to measure relative pressure changes due to blockages in the breath sampling tube. Optionally, the breath sampling device may be adapted to measure pressure rate of change due to blockages in the breath sampling tube. The pressure sensor may be preset at relatively low threshold values, for example in the range of 30 mbars to 70 mbars, so as to increase sensitivity to relative pressure changes in the sampling port. Optionally, the pressure sensor may be preset at relatively high pressure rates of change, for example 10 mbar per 50 msec being indicative of a blockage. The breath sampling device may be further adapted to not be susceptible to sudden pressure changes as are typically experienced in aircraft during flight, which would be misinterpreted as a blockage.

In an embodiment of the invention, the controller, upon pressure sensor measurement of the preset threshold value, or optionally, the preset pressure rate of change, deactivates a pump in the breath sampling device which is used to create a negative pressure in the breath sampling tube and the sampling port. Optionally, substantially at the same time as, or following, pump deactivation the controller initiates a valve comprised in the breath sampling device, adapted to allow air, or optionally another gas, to flow into a line interconnecting the breath sampling tube and the pump. Optionally, the valve may be positioned external to the breath sampling device, and may be adapted to allow air, or optionally another gas, to flow into the lower pressure section of the breath sampling tube and into the line interconnecting the breath sampling tube with the pump. This may, at least partially prevent the blockage from reaching the breath sampling device.

In some embodiments of the invention, the valve comprises a solenoid valve, which is adapted, upon indication of a pressure reaching a predetermined threshold value or optionally, upon reaching a predetermined rate of change of pressure, to cyclically toggle between a NORMAL mode of operation and an AUTO-ZERO mode of operation while the pump is deactivated. This enables air, or optionally another gas, to flow into the lower pressure section of the breath sampling tube, equalizing the pressure on both sides of the blockage, for example between the blockage and the pump. This may, at least partially, prevent the blockage from reaching the breath sampling device. Test results show that the breath sampling device comprising the solenoid valve and the fast response pressure sensor may reduce the amount of liquid entering the breath sampling tube, when an airway adapter has its sampling port submerged in liquid, to between 200 ul (microliter) and 400 ul.

According to an embodiment of the invention, there is provided a method for removing the blockage from the breath sampling tube. The controller, after a predetermined interval of time, during which pressure in the breath sampling tube is equalized and the liquid is assumed to have been collected by the liquid collection means, which may be several seconds, for example 5 to 10 seconds, will reactivate the pump in the breath sampling device to recreate a negative pressure in the breath sampling tube. If the pressure threshold is not reached after a predetermined time interval during which the pump is in operation, normal operation is assumed. If the pressure threshold is reached, the pump continues to operate while the threshold of the pressure sensor is increased in increments ranging from 10 mbar to 50 mbar until the blockage is cleared. Optionally, prior to increasing the threshold, the pump may be turned off and the pressure in the breath sampling tube equalized again. After waiting the predetermined interval of time following detection of a blockage, the pump is reactivated. If the blockage is not cleared, only then is the threshold increased. Optionally, this step may be performed one or more times between one or more threshold increases. Upon reaching a maximum pressure threshold, for example 120 mbar, if the blockage has not been cleared, the controller turns off the pump. The breath sampling device is then adapted to display a blockage alarm, and the breath sampling tube may be replaced.

According to some embodiments, there is provided a breath sampling device comprising a controller adapted to initiate a signal to trigger a valve functionally associated with a breath sampling tube upon said controller receiving a signal indicating a blockage in the breath sampling tube. The valve may be adapted to facilitate an increase of pressure within the breath sampling tube between the blockage and a pump functionally associated with the breath sampling tube. The valve may be adapted to facilitate an increase of pressure within the breath sampling tube between the blockage and the pump by allowing air into the breath sampling tube between the blockage and the pump.

The controller may further be adapted to initiate a signal to deactivate a pump functionally associated with the breath sampling tube.

The signal indicating a blockage in the breath sampling tube may be indicative of a pressure measurement within said breath sampling tube reaching a predetermined threshold value. The signal indicating a blockage in the breath sampling tube may be indicative of a pressure change rate within said breath sampling tube reaching or exceeding a predetermined threshold value.

The valve may be a solenoid valve. The solenoid valve may be adapted to toggle (for example, cyclically toggle) between a NORMAL mode of operation and an AUTO-ZERO mode of operation, while the pump is deactivated in these modes of operation, which is adapted to allow air into the breath sampling tube between the blockage and the pump.

According to further embodiments of the invention, there are provided devices, such as sampling tubes and airway adaptors, which are adapted to reduce the velocity at which the undesired liquids flow into the sampling port and thus, facilitate the collection of undesired liquid in collection means and thereby reduce the occurrences of blockages.

In accordance with some embodiments of the invention, the sampling port may include a restrictor adapted to reduce the velocity at which the undesired liquids flow into the sampling tube and to reduce the quantity of liquid that is able to enter the sampling tube during the period up to its detection. This also facilitates the collection of undesired liquid in collection means.

The restrictor may have a restricting hole of a certain diameter adapted to reduce the velocity at which liquids flow into the sampling port. Additionally, the diameter is adapted to maintain the waveform of the breath samples so as enable the breath sampling device to substantially accurately measure and analyze the breath samples. The restrictor is manufactured preferably of a very hydrophobic material, such as, for example, Teflon, which exhibits very hydrophobic characteristics, so as to reduce the probability of thick liquids entering a breath sampling tube which connects at one end to the sampling port.

Test results show that the use of a sampling port which includes a restrictor, in combination with the breath sampling device comprising a fast response pressure sensor and a solenoid valve, may reduce the amount of liquid entering the breath sampling tube to less than 100 ul, well below the more than 1 cc which may enter the line using the current methods known in the art. The test results are based on the use of a restrictor with incurred pressure drop of 15 mbar at 50 ml/min. The final amount of liquid entering the breath sampling tube is dependent on the restrictor size, the speed of detection and reaction by the breath sampling device, the position of the restrictor within the sampling port, and threshold level, or optionally, the pressure rate of change, of the pressure sensor.

In some embodiments of the invention, the sampling port comprises one or more openings in the outlet tube, external to the airway adapter and exposed to the ambient. The openings are adapted to allow an increase in the rate of air leakage into the outlet tube in reaction to an increase in the pressure differential between the ambient and the outlet tube. The increase in the pressure differential is the result of an increase in the negative pressure inside the breath sampling tube due to liquid entering the sampling port and being pulled in by the suctioning action of a pump in the breath sampling device. As the negative pressure increases, more air flows in through the openings in the form of bubbles, diluting and slowing down the influx of liquid, consequently reducing the quantity of liquid reaching the breath sampling tube. Additionally, the openings are adapted to allow air to leak into the outlet tube while maintaining the waveform of the breath samples so as enable the breath sampling device to substantially accurately measure and analyze the breath samples. In other words, the openings are made small enough to prevent or at least reduce the dilution of the sampled breath with ambient air. Test results show that the use of a sampling port with small openings in the outlet, in combination with the breath sampling device comprising a fast response pressure sensor and a solenoid valve, may reduce the amount of liquid entering the breath sampling tube, when an airway adapter has its sampling port submerged in liquid, to less than 100 ul, well below the more than 1 cc which may enter the line using the current methods known in the art. The test results are based on the openings having a total leak rate of 1/400 relative to the actual flow rate of the breath sampling device, which is typically 20 ml/min-50 ml/min.

In some embodiments, there is provided an airway adapter comprising a restrictor located in proximity to a connection point between the airway adapter and a breath sampling tube. The restrictor may be located inside a sampling port. The restrictor may be adapted to reduce the flow rate of liquids entering the breath sampling tube. The restrictor may be manufactured from a hydrophobic material. The restrictor may have a uniform inner diameter and comprises a restricting hole of the same diameter. The restrictor may have a restricting hole of lesser diameter than the inner diameter.

In some embodiments, there is provided a breath sampling tube comprising a restrictor located in proximity to a connection point between the breath sampling tube and an airway adapter. The restrictor may be adapted to reduce the flow rate of liquids entering the breath sampling tube. The restrictor may be manufactured from a hydrophobic material. The restrictor may have a uniform interior diameter. The restrictor includes a restricting hole adapted to reduce the velocity at which liquids flow into the sampling port. The restricting hole may be of a same diameter as the inner diameter, or may be of a lesser diameter than the inner diameter.

In some embodiments, there is provided a breath sampling device comprising an airway adapter including one or more openings located near a connection point between said airway adapter and a breath sampling tube.

In some embodiments, there is provided a breath sampling-tube, including one or more openings located near a connection point between the breath sampling tube and an airway adapter.

The openings may be located in a sampling port. The openings are adapted to allow inflow of air to reduce the flow rate of liquids entering the breath sampling tube.

In some embodiments, there is provided a breath sampling system, comprising a controller adapted to initiate a signal to toggle a valve functionally associated with a breath sampling tube upon said controller receiving a signal indicating a blockage in the breath sampling tube and an airway adapter comprising a restrictor located in proximity to a connection point between the airway adapter and a breath sampling tube.

In some embodiments, there is provided a breath sampling system, comprising a controller adapted to initiate a signal to toggle a valve functionally associated with a breath sampling tube upon said controller receiving a signal indicating a blockage in the breath sampling tube and breath sampling tube comprising a restrictor located in proximity to a connection point between the breath sampling tube and an airway adapter.

In some embodiments, there is provided a breath sampling system comprising a controller adapted to initiate a signal to toggle a valve functionally associated with a breath sampling tube upon said controller receiving a signal indicating a blockage in the breath sampling tube and an airway adapter including one or more openings located near a connection point between said airway adapter and a breath sampling tube.

In some embodiments, there is provided a breath sampling system comprising a controller adapted to initiate a signal to toggle a valve functionally associated with a breath sampling tube upon said controller receiving a signal indicating a blockage in the breath sampling tube and an airway adapter including one or more openings located near a connection point between said airway adapter and a breath sampling tube.

In some embodiments, there is provided a breath sampling system comprising a controller adapted to initiate a signal to toggle a valve functionally associated with a breath sampling tube upon said controller receiving a signal indicating a blockage in the breath sampling tube and a breath sampling tube including one or more openings located near a connection point between the breath sampling tube and an airway adapter.

BRIEF DESCRIPTION OF THE FIGURES

Examples illustrative of embodiments of the invention are described below with reference to figures attached hereto. In the figures, identical structures, elements or parts that appear in more than one figure are generally labeled with a same numeral in all the figures in which they appear. Dimensions of components and features shown in the figures are generally chosen for convenience and clarity of presentation and are not necessarily shown to scale. The figures are listed below.

DETAILED DESCRIPTION

Figure 1:
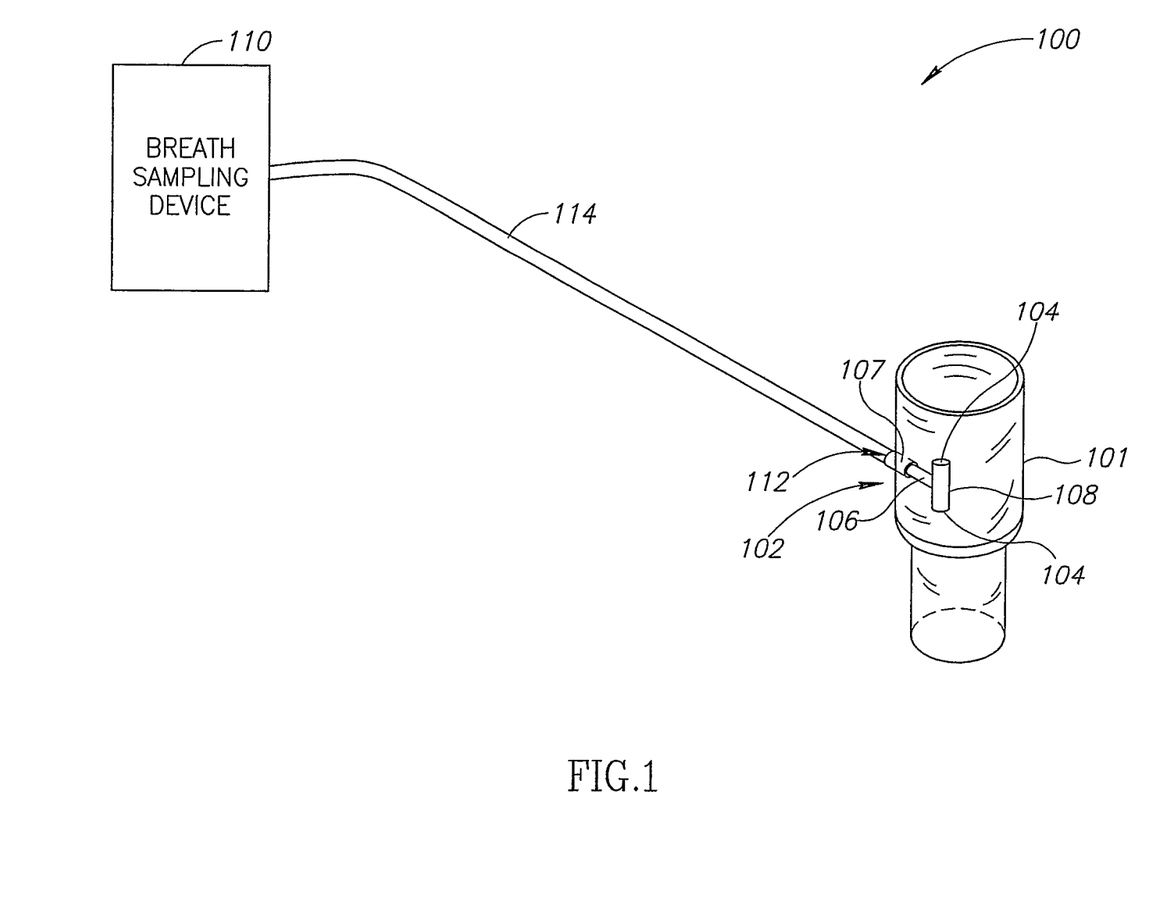
FIG. 1 schematically illustrates a typical breath sampling system used in side-stream Capnography.

Reference is made to FIG. 1 which schematically illustrates an exemplary breath sampling system (100) used in side-stream Capnography, known in the art. Breath sampling system (100), which may hereinafter also be referred to as "sampling system", may also be used in an embodiment of the invention.

Exhaled breath sample collection is done through an airway adapter (101), essentially a tube adapted to connect to a patient airway tube (not shown) at one end, and to a patient respiratory mechanism (not shown) such as, for example, a nasal or oral cannula, an endotracheal tube or intubating tube, and the like, at the other end. Airway adapter (101) includes one sampling port (102), as shown, although other embodiments of the invention may include a plurality of sampling ports. Sampling port (102) is adapted to capture samples of exhaled breath while having a minimum effect on the waveform of the exhaled breath samples.

Sampling port (102) has a "T-shaped" configuration and comprises an inlet tube (108) and an outlet tube (106). Outlet tube (108) extends from the exterior of airway adapter (101) into the air passageway in the direction of the center of airway adapter (101), and inlet tube (108) extends essentially perpendicular to outlet tube (106) and parallel to the direction of airflow in airway adapter (101). Inlet tube (108) includes two inlets (104) through which exhaled breath samples are drawn into sampling port (102). The breath samples then flow from inlet tube (108) into outlet tube (106). Outlet tube (106) includes an outlet (112) through which the breath samples are then drawn out from sampling port (102) into a breath sampling tube (114). A connector (107) extends from outlet tube (106) and is adapted to fittingly receive one end of breath sampling tube (114). In some embodiments of the invention, sampling port (102) and sampling inlets (104) may be configured in airway adapter (101) in varying numbers, shapes and lengths, as well as in different positions within airway adapter (101).

Breath sampling tube (114), which is adapted to have minimum effect on the waveform of the exhaled breath samples, is connected at one end to sampling port (102) and at the other end to a breath sampling device (110). Breath sampling tube (114) generally further includes one or more liquid collection means to limit the possible accumulation of liquids in tube (114). Accumulation of liquids in the tube may result in blockage of tube (114), thereby interfering with the continuous, smooth flow of the exhaled breath sample, or which may subsequently reach breath sampling device (110) possibly damaging its components. Numerous methods to limit the accumulation of liquids in breath sampling tube (114) are known in the art, several of which were described above.

Breath sampling device (110), which may be a Capnograph, is connected to one end of breath sampling tube (114), opposite the end connected to sampling port (102). Breath sampling device (110) comprises a pump (not shown) which may be, for example, a diaphragm pump, which when operated creates a suctioning force such that the pressure at the entrance to breath sampling device (110), as well as along breath sampling tube (114) and in sampling port (102) will be lower than in airway adapter (101). The magnitude of the lower pressure, which may also be referred to as an increased negative pressure, is a function of the distance from the pump, the magnitude decreasing as the distance from the pump increases. This low pressure gradient causes the exhaled breath samples in airway adapter (101) to flow into inlets (104) of sampling port (102) and subsequently flow through breath sampling tube (114) to breath sampling device (110), which is adapted to perform measurement and analysis of the exhaled breath samples.

Figure 2A:
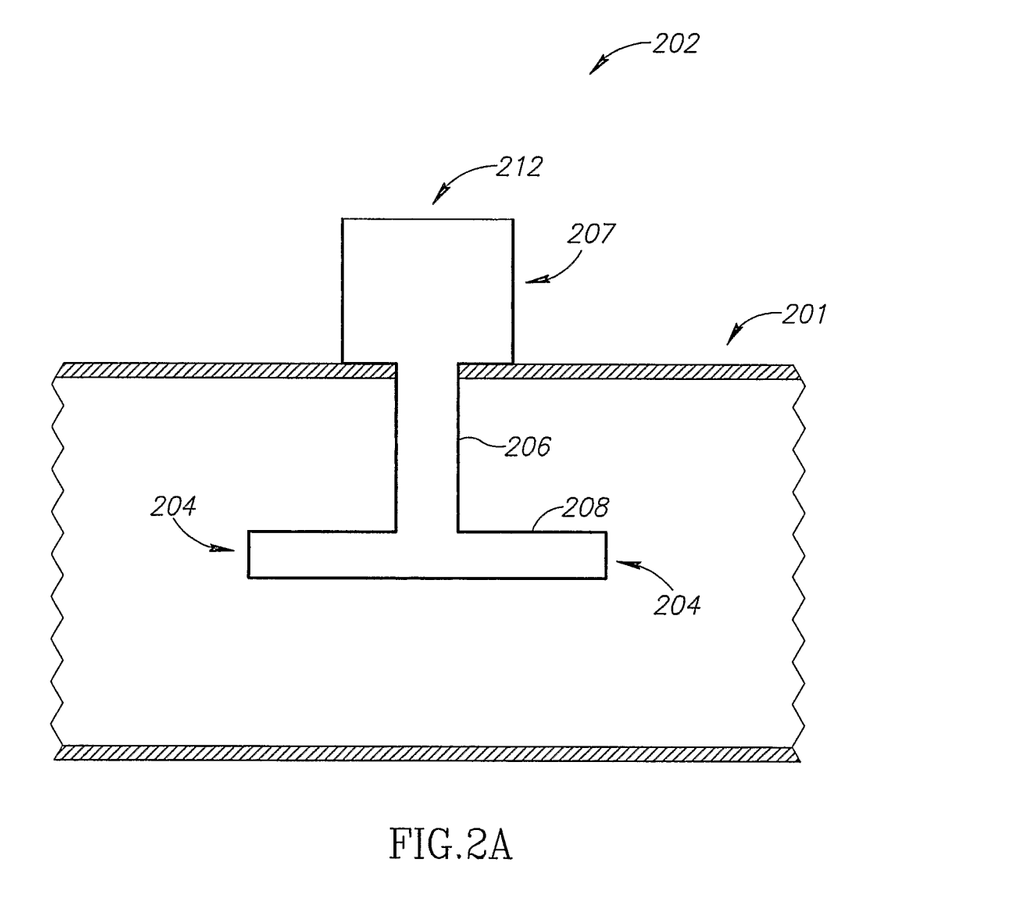
FIG. 2a schematically shows a side view of an exemplary sampling port in an exemplary airway adapter, in accordance with an embodiment of the invention.
Figure 2B:
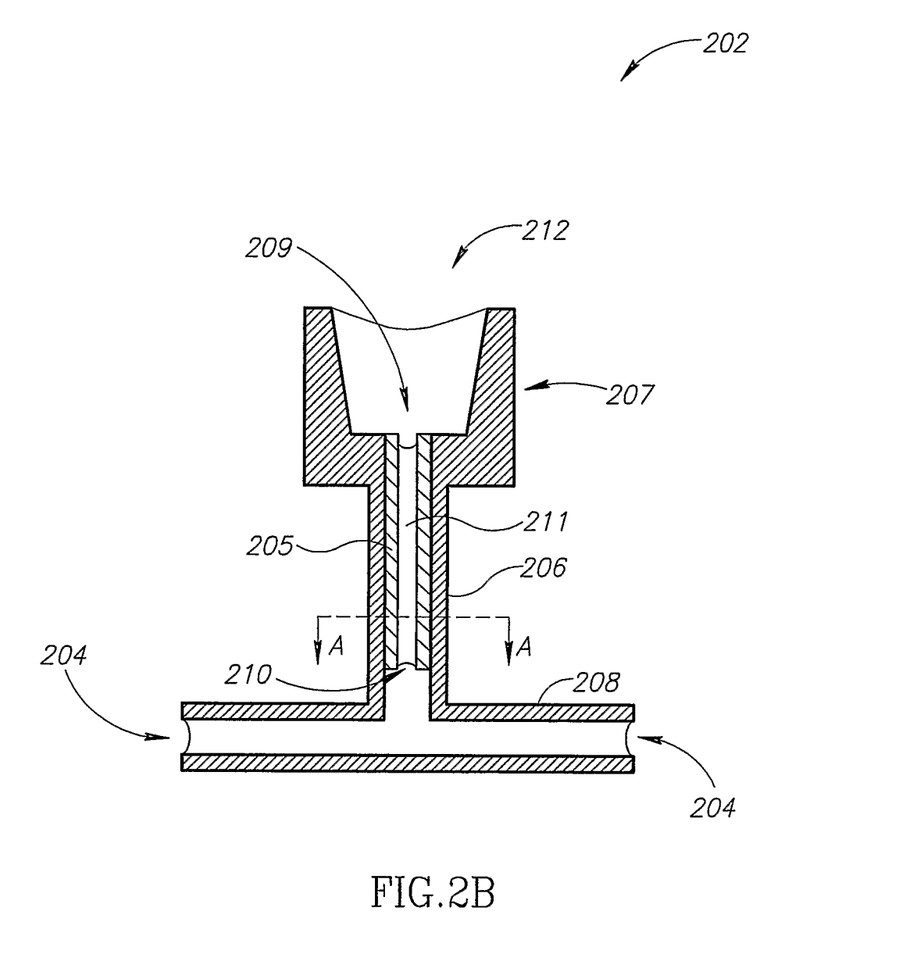
FIG. 2b schematically shows a cross-sectional side view of the sampling port shown in FIG. 2a comprising a restrictor, in accordance with an embodiment of the invention.

Reference is made to FIG. 2a which schematically shows a side view of an exemplary sampling port (202) in an exemplary airway adapter (201), in accordance with an embodiment of the invention. Reference is also made to FIG. 2b which schematically shows a cross-sectional side view of sampling port (202) in FIG. 2a, comprising a restrictor (205), in accordance with an embodiment of the invention. Sampling port (202) and airway adapter (201) may be substantially similar or the same to that shown in FIG. 1 at (102) and (101), respectively.

Sampling port (202) has a "T-shaped" configuration and comprises an inlet tube (208) and an outlet tube (206), outlet tube (208) perpendicularly extending from the center of inlet tube (208) to a connector (207). Inlet tube (208) includes two inlets (204) through which exhaled samples are drawn into sampling port (202) from airway adapter (201). The breath samples then flow from inlet tube (208) into outlet tube (206). Outlet tube (206) includes an outlet (212) through which the breath samples are then drawn out from sampling port (202) into a breath sampling tube (not shown). The inside diameter of inlet tube (208) and outlet tube (206) is typically 1 mm-2 mm so as to have minimum effect on the waveform of the exhaled breath samples, although the inside diameter may be of any dimension which has minimum effect on the waveform of the exhaled breath samples.

A connector (207) extends from outlet tube (206) and is adapted to fittingly receive one end of the breath sampling tube. Connector (207) is preferably cylindrical in shape, and includes an opening (209) at one end, where outlet tube (208) and connector (207) meet. The inner diameter and the shape of connector (207) are adapted so that the breath sampling tube may be inserted through outlet (212) and firmly coupled to sampling port (202), opening (209) properly aligning with the opening of the breath sampling tube so as to have minimum effect on the waveform of the exhaled breath samples. Connector (207) is formed as an integral part of sampling port (202), although in other embodiments of the invention, connector (207) may not be integrally formed as part of sampling port (202) and may be attached to outlet tube (208).

Sampling port (202) is generally made from a plastic material, for example PVC, but may also be made from a non-plastic material. The material characteristics should generally be of a hydrophobic nature so as to limit the entry of liquids into sampling port (202) and subsequently into the breath sampling tube.

To further enhance the hydrophobic nature of sampling port (202), a restrictor (205) is fitted inside outlet tube (206). This further limits the possibility of liquids flowing from sampling port (202) into the breath sampling tube. Restrictor (205) is preferably a cylindrical tube fabricated from a highly hydrophobic material such as, for example, Teflon, although other hydrophobic materials may be used. The length and inner diameter of restrictor (205) are adapted so that the effect on the waveform of the exhaled breath sample is maintained to a minimum yet has an effect on fluids of greater viscosity which experience a relatively large reduction in the velocity of the flow as they encounter restrictor (205) and flow through a restricting hole (210) and on through a restrictor bore (211) towards opening (209). As a result, liquids which have entered sampling port (202) through inlets (204) are slowed down as they pass from inlet tube (208) through restrictor (205) in outlet tube (206) toward the breath sampling tube.

In accordance with other embodiments of the invention, sampling port (202) may be configured in other shapes, for example, such as "L-shape", off-center "T-shape", or may have only one inlet or more than two inlets. Furthermore, the dimensions of all elements, including inlets (204), inlet tube (208), outlet tube (206), restrictor (205), and connector (207) may be varied. Additionally, the position of restrictor (205) may be varied within sampling port (202).

Figure 3A:
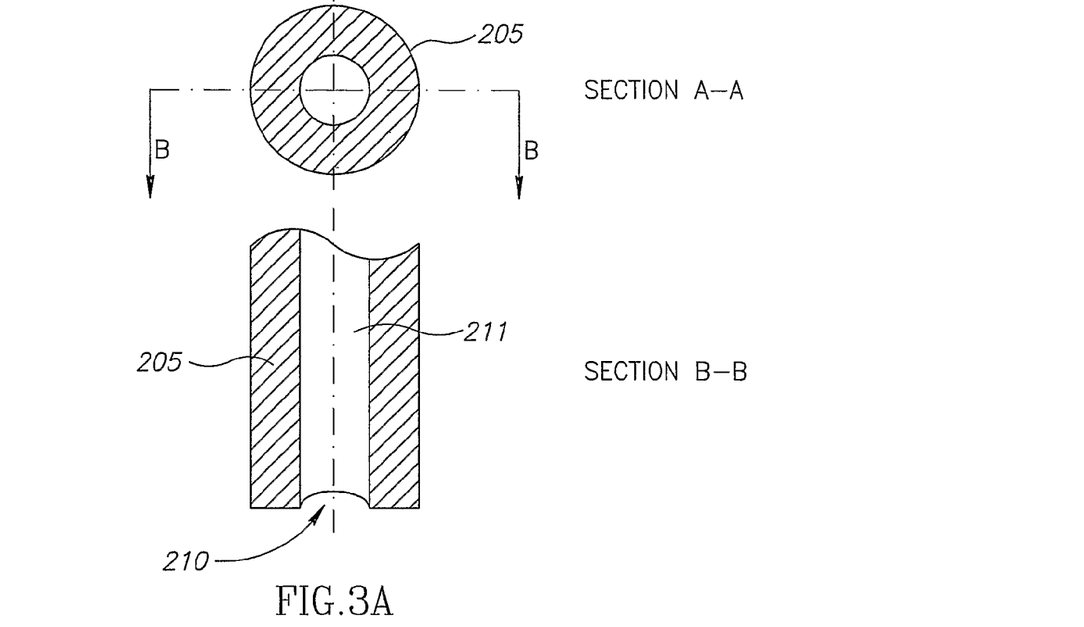
FIG. 3a schematically illustrates cross-sectional views A-A and B-B of the exemplary restrictor shown in FIG. 2b, in accordance with an embodiment of the invention.

Reference is made to FIG. 3a, which schematically illustrates cross-sectional views A-A and B-B of exemplary restrictor (205) shown in FIG. 2, in accordance with an embodiment of the invention. Restrictor (205) is cylindrical in shape and comprises restricting bore (211) of uniform inner diameter along the whole length.

Figure 3B:
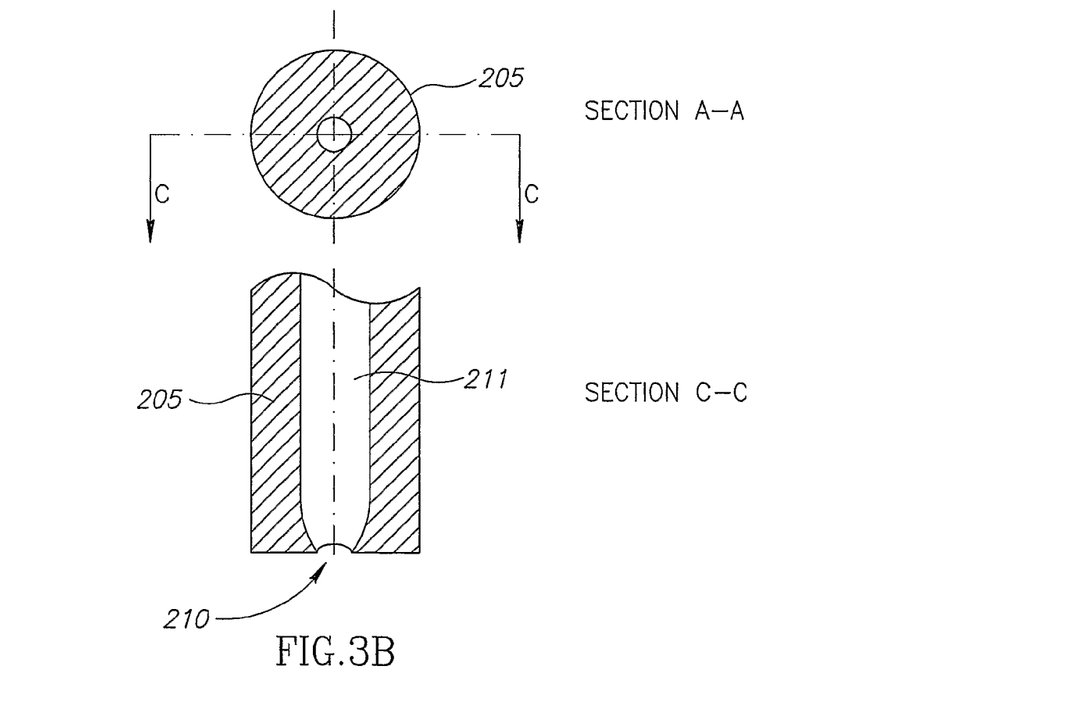
FIG. 3b schematically illustrates cross-sectional views A-A and C-C of the exemplary restrictor shown in FIG. 2b, in accordance with another embodiment of the invention.

Reference is made to FIG. 3b which schematically illustrates cross-sectional views A-A and C-C of exemplary restrictor (205) shown in FIG. 2, in accordance with another embodiment of the invention. Restrictor (205) is cylindrical in shape and comprises restrictor bore (211) of uniform inner diameter along the major part of its length, the inner diameter gradually tapering down to a smaller diameter at restricting hole (210). Restricting hole (210) is adapted have a minimum effect on the waveform of the exhaled breath samples and is further adapted to reduce the entry of relatively large amounts of liquid into the breath sampling tube by reducing the liquid flow velocity.

Figure 4:
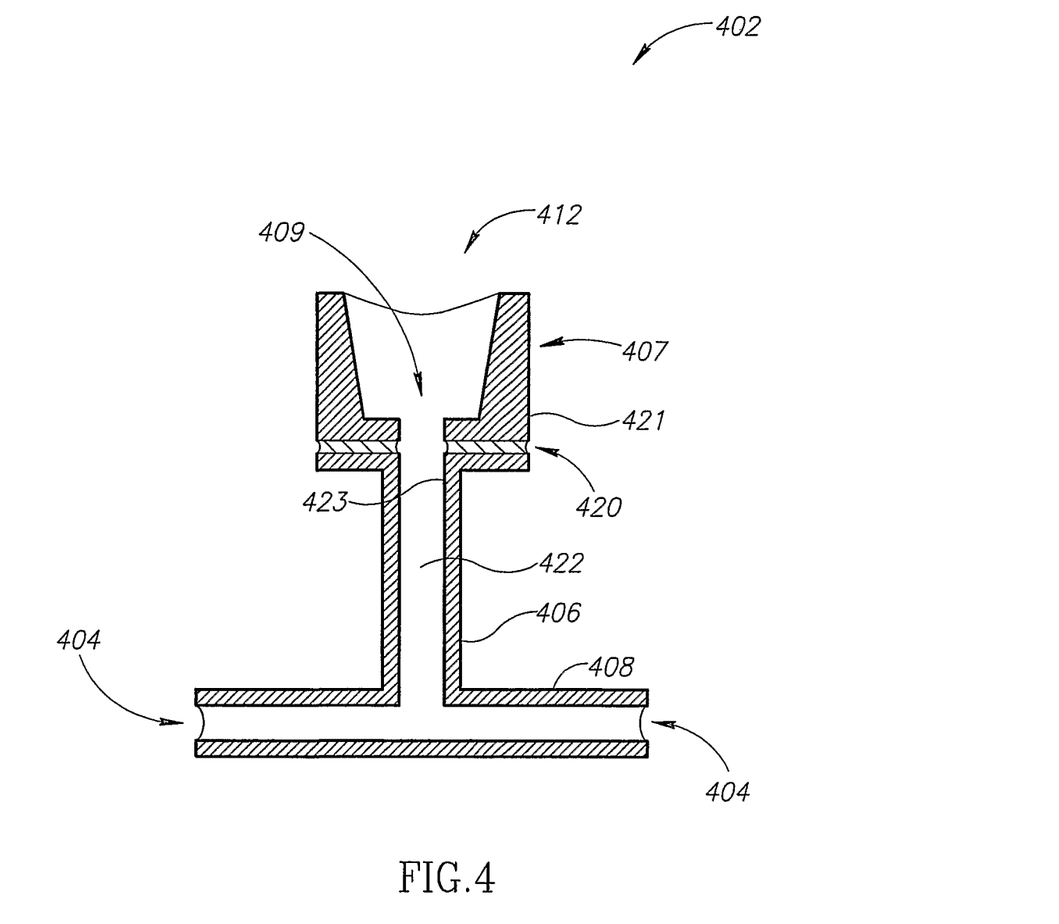
FIG. 4 schematically shows a cross-sectional side view of an exemplary sampling port comprising openings for air leaks, in accordance with an embodiment of the invention.

Reference is made to FIG. 4, which schematically shows a cross-sectional side view of an exemplary sampling port (402) comprising openings (420) for air leaks, in accordance with an embodiment of the invention. Sampling port (402) may be the same or substantially similar to that shown in FIG. 2a at (202). Sampling port (402) has a "T-shaped" configuration and comprises an inlet tube (408) and an outlet tube (406), outlet tube (406) perpendicularly extending from the center of inlet tube (408) to a connector (407). Inlet tube (408) includes two inlets (404) through which exhaled samples are drawn into sampling port (402). The breath samples then flow from inlet tube (408) into outlet tube (406). Outlet tube (406) includes an outlet (412) through which the breath samples are then drawn out from sampling port (402) into a breath sampling tube (not shown). The inside diameter of inlet tube (408) and outlet tube (406) is typically 1 mm-2 mm so as to have minimum effect on the waveform of the exhaled breath samples, although the inside diameter may be of any dimension which has minimum effect on the waveform of the exhaled breath samples.

A connector (407) extends from outlet tube (406) and is adapted to fittingly receive one end of the breath sampling tube. Connector (407) is preferably cylindrical in shape, and includes an opening (409) at one end, where outlet tube (408) and connector (407) meet. The inner diameter and the shape of connector (407) are adapted so that the breath sampling tube may be inserted through outlet (412) and firmly coupled to sampling port (402), opening (409) properly aligning with the opening of the breath sampling tube so as to have minimum effect on the waveform of the exhaled breath samples. Connector (407) is formed as an integral part of sampling port (402), although in other embodiments of the invention, connector (407) may not be integrally formed as part of sampling port (402) and may be attached to outlet tube (408).

Sampling port (402) is generally made from a plastic material, for example PVC, but may also be made from a non-plastic material. The material characteristics should generally be of a hydrophobic nature, so as to limit the entry of liquids into sampling port (402) and subsequently into the breath sampling tube.

To further enhance the hydrophobic nature of sampling port (402), two small bores (420) extend from an external wall (421) of sampling port (402) to the inner wall of outlet tube (423). The dimensions of bores (420) are adapted to allow air to leak into conduit (422) of outlet tube (406) at a rate which has minimum effect on the waveform of the exhaled breath samples. Furthermore, the dimensions of bores (420) are adapted to allow an increase in the rate of air leakage into conduit (422) in reaction to an increase in a pressure differential between the ambient and conduit (422). In some embodiments of the invention, the sampling port may comprise one, or more than two, small bores. The bores may extend from the external wall to the inner wall from any direction, and optionally, at any angle.

Figure 5:
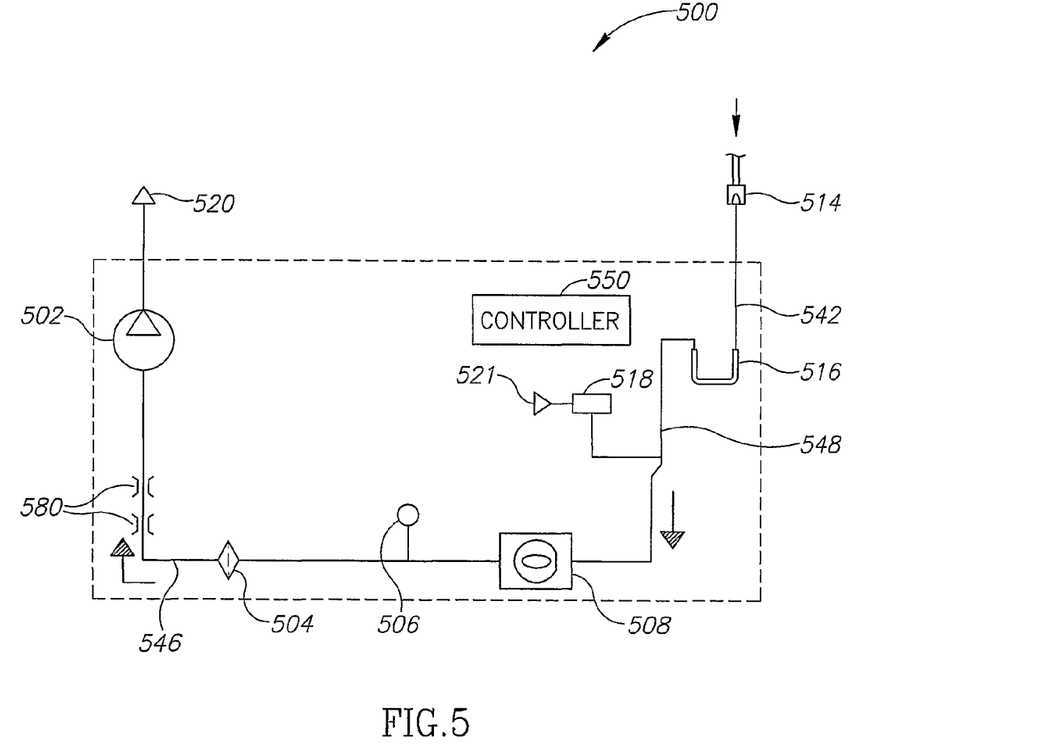
FIG. 5 schematically shows a block diagram for an exemplary breath sampling device, in accordance with an embodiment of the invention.

Reference is made to FIG. 5, which schematically shows a block diagram for an exemplary breath sampling device (500), in accordance with an embodiment of the invention. It may be appreciated by a person skilled in the art that the components shown, their interconnection, and the description provided for the operation of the breath sampling device is for illustrative purposes, and in no way are intended to be limiting in any form.

Breath sampling device (500) is adapted to measure and analyze exhaled breath samples received through a breath sampling tube (514), which may be similar or the same to that shown in FIG. 1 at (114). The breath sampling tube may include a sampling port. A Nafion tube (516), adapted to absorb humidity in the breath samples, is serially connected to breath sampling tube (514) through a tube (542), which connects to an inlet port (not shown) in breath sampling device (500). A sensor assembly (508), adapted to measure the waveform characteristic of the exhaled breath samples for processing by a controller (550), is serially connected to Nafion tube (516) through tube (548). In accordance with an embodiment of the invention, a valve (518) is connected to tube (548) and is adapted to allow breath samples to flow through tube (548) under normal operating condition, and is further adapted to allow air, or optionally another gas, to flow into tube (548) when a blockage is detected in breath sampling tube (514).

Controller (550) is adapted to process the information received from sensor assembly (508) for display purposes and to perform control functions, which include, for example, opening of valve (518) and deactivation and activation of a pump (502). A pressure sensor (506) is adapted to monitor the pressure in breath sampling tube (514) by measuring the pressure in tube (546), which serially connects sensor assembly (508) to pump (502), and provides this information as an input to controller (550). Pressure sensor (506) is a fast response pressure sensor and is adapted to measure relative pressure changes. Optionally, the pressure sensor is adapted to measure pressure rate of change. Pump (502), which may be a diaphragm pump, is adapted to create a suctioning force such that the pressure at the entrance to breath sampling device (500), as well as along breath sampling tube (514), will be lower than in the airway adapter (not shown) connected at the other end of breath sampling tube (514). Breath sampling device (500) also comprises numerous filters (504) adapted to restrict particles from entering pump (502) and numerous restrictors (580) adapted to regulate flow.

Pump (502) is operating so that exhaled breath samples are flowing through breath sampling tube (514) into the breath sampling device (500). The arrows depict the direction of flow of the breath samples during normal breath sampling operation. Typical flow rates for the exhaled breath samples may be between 10 ml/min and 200 ml/min, for example, 10 ml/min to 20 ml/min, 21 ml/min to 30 ml/min, 31 ml/min to 40 ml/min, 41 ml/min to 50 ml/min, 51 ml/min to 60 ml/min, 61 ml/min to 70 ml/min. The breath samples flow through tube (542) into Nafion tube (516) where remnants of humidity in the breath samples are absorbed. The breath samples flow through tube (548) to the sensor assembly (508), where the characteristics of the waveform of the exhaled breath samples are measured. The pressure sensor (506), which is constantly measuring the pressure in tube (546), and/or optionally the rate of change of the pressure in the tube, is set at a predetermined threshold and/or rate of change, to indicate a blockage in the breath sampling tube (514). The threshold may be set at predetermined values ranging between 20 mbar and 120 mbars, for example, values in the range between 20 mbar to 40 mbar, 41 mbar to 60 mbar, 61 mbar to 80 mbar, 81 mbar to 100 mbar, 101 mbar to 120 mbar. Optionally, the pressure rate of change may be set at a relatively high value, for example, 10 mbar per 50 msec, indicative of a blockage. The breath samples continue to flow through tube (546) in the direction of the pump (502) and subsequently to an exhaust (520) in the breath sampling device.

When a blockage is detected in the breath sampling tube (514), controller (550) sends a signal deactivating the pump (502). By deactivating the pump, the blockage is prevented from being drawn further into the breath sampling tube. Substantially at the same time as, or optionally following, deactivation of the pump, controller (550) opens a valve connected to tube (548). Air, or optionally another gas, flows through intake valve (521) into tube (548) and thereon to fill tubes (546) and (542), and breath sampling tube (514), as there is a lower pressure in all the tubes. The air, or optionally another gas, fills the tubes, including the breath sampling tube all the way to the blockage, equalizing the pressure on both sides of the blockage.

The controller, after a predetermined interval of time, during which pressure in the breath sampling tube is equalized and the liquid is assumed to have been collected by the liquid collection means, reactivates the pump in the breath sampling device to recreate a negative pressure in the breath sampling tube. The predetermined interval of time may be several seconds, for example 5 to 10 seconds. If the pressure threshold is not reached after a predetermined time interval during which the pump is in operation, normal operation is assumed. If the pressure threshold is reached, the pump continues to operate while the threshold of the pressure sensor is increased in increments ranging from 10 mbar to 50 mbar, until the blockage is cleared. Optionally, prior to increasing the threshold, the pump may be turned off and the pressure in the breath sampling tube equalized again. After waiting the predetermined interval of time following detection of a blockage, the pump is reactivated. If the blockage is not cleared, only then is the threshold increased. Optionally, this step may be performed one or more times between one or more threshold increases. Upon reaching a maximum pressure threshold, for example 120 mbar, if the blockage has not been cleared, the controller turns off the pump. The breath sampling device is then adapted to display a blockage alarm, and the breath sampling tube may be replaced.

Figure 6A:
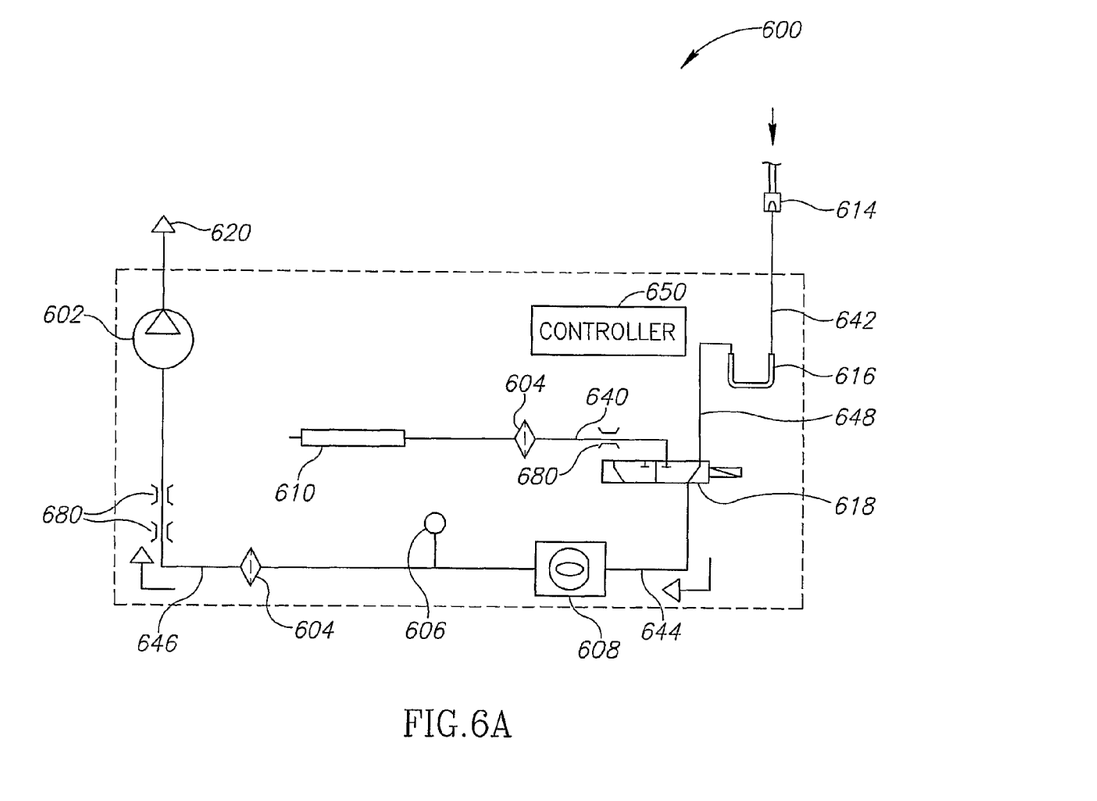
FIG. 6a schematically illustrates a block diagram of a breath sampling device in NORMAL mode of operation in accordance with another embodiment of the invention.
Figure 6B:
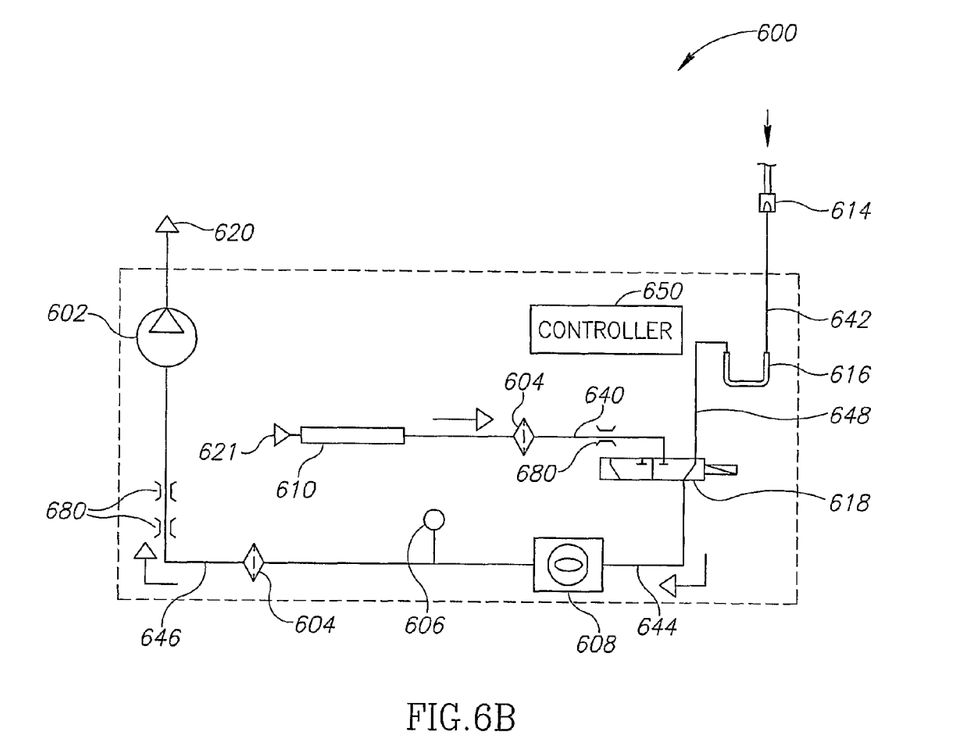
FIG. 6b schematically illustrates a block diagram of the breath sampling device of FIG. 6a in AUTO-ZERO mode of operation, in accordance with another embodiment of the invention.

Reference is made to FIGS. 6a and 6b which schematically show block diagrams of a breath sampling device (600), in accordance with another embodiment of the invention. Breath sampling device (600) may be similar or the same to that shown in FIG. 1 at (100). The schematic diagram depicted in FIG. 6a is for a NORMAL mode of operation wherein the breath sampling device (600) is measuring and analyzing exhaled breath samples under normal conditions. FIG. 6b is for an AUTO-ZERO mode of operation, wherein the breath sampling device (600) performs self-zeroing for calibration purposes. It may be appreciated by a person skilled in the art that the components shown, their interconnection, and the description provided for the operation of the breath sampling device are for illustrative purposes, and in no way are intended to be limiting in any form.

Breath sampling device (600) is adapted to measure and analyze exhaled breath samples received through a breath sampling tube (614) which may be similar or the same to that shown in FIG. 1 at (114). A Nafion tube (616), adapted to absorb humidity in the breath samples, is serially connected to breath sampling tube (614) through a tube (642), which connects to an inlet port (not shown) in the breath sampling device (600). A solenoid valve (618), adapted to toggle between the NORMAL mode flow path and the AUTO-ZERO mode flow path in the breath sampling device (600), the modes described in greater detail below, comprises three ports (not shown); two are parallel inlet ports and one is an outlet port. One inlet port is connected to Nafion tube (616), and subsequently to breath sampling tube (614), through tube (648) so that the exhaled breath samples flow into this inlet port and out the outlet port of solenoid valve (618), and through a tube (644) connected to the outlet port, to a sensor assembly (608). The second inlet port is connected to a scrubber (610) through a tube (640) so that air drawn into breath sampling device (600) and passing through scrubber (610) flows into this inlet port and out the outlet port of solenoid valve (618), and through tube (644) to sensor assembly (608). Solenoid valve (614), depending on the mode of operation, is adapted to connect either the flow path from breath sampling tube (614) to sensor assembly (608), which is the NORMAL mode of operation, or to connect the flow path from scrubber (610) to sensor assembly (608), which is the AUTO-ZERO mode of operation.

Sensor assembly (608), adapted to measure the waveform characteristic of the exhaled breath samples for processing by a controller (650), is serially connected to the outlet port of solenoid valve (618) through tube (644). Controller (650) is adapted to process the information received from sensor assembly (608) for display purposes and to perform control functions, which include, for example, toggling of solenoid valve (618) and deactivation/activation of a pump (602). A pressure sensor (606) is adapted to monitor the pressure in breath sampling tube (614) by measuring the pressure in tube (606), which serially connects sensor assembly (608) to pump (602), and provides this information as an input to controller (650). Pressure sensor (606) is a fast response pressure sensor and is adapted to measure relative pressure changes. Optionally, the pressure sensor is adapted to measure pressure rate of change. Pump (602), which may be a diaphragm pump, is adapted to create a suctioning force such that the pressure at the entrance to breath sampling device (600), as well as along breath sampling tube (614), will be lower than in the airway adapter (not shown) connected at the other end of breath sampling tube (614). Scrubber (610) is adapted to clean $CO_2$ (carbon dioxide) from air drawn into breath sampling device (600) for zero-point calibration purposes through air intake (621). Breath sampling device (600) also comprises numerous filters (604) adapted to restrict particles from entering pump (602) and numerous restrictors (680) adapted to regulate flow.

Reference is made to FIG. 6a, which depicts the NORMAL mode of operation. The pump (602) is operating so that exhaled breath samples are flowing through the breath sampling tube (614) into the breath sampling device (600). The arrows depict the direction of flow of the breath samples during normal breath sampling operation. Typical flow rates for the exhaled breath samples may be between 10 ml/min and 200 ml/min, for example, 10 ml/min to 20 ml/min, 21 ml/min to 30 ml/min, 31 ml/min to 40 ml/min, 41 ml/min to 50 ml/min, 51 ml/min to 60 ml/min, 61 ml/min to 70 ml/min. The breath samples flow through tube (642) into Nafion tube (616) where remnants of humidity in the breath samples are absorbed. The breath samples flow through tube (648) through solenoid valve (618), which is toggled in the position associated with NORMAL, and through tube (644) to sensor assembly (608), where the characteristics of the waveform of the exhaled breath samples are measured. Pressure sensor (606), which is constantly measuring the pressure in tube (646), is set at a predetermined threshold to indicate a blockage in breath sampling tube (614). The threshold may be set at predetermined values ranging between 20 mbar and 120 mbars, for example, values in the range between 20 mbar to 40 mbar, 41 mbar to 60 mbar, 61 mbar to 80 mbar, 81 mbar to 100 mbar, 101 mbar to 120 mbar. Optionally, the pressure rate of change may be set at a relatively high value, for example, 10 mbar per 50 msec, indicative of a blockage. The breath samples continue to flow through tube (646) in the direction of pump (602) and subsequently to an exhaust (620) in the breath sampling device.

Reference is made to FIG. 6b, which depicts the AUTO-ZERO mode of operation. In this mode, in which the breath sampling device (600) is being calibrated, the solenoid valve (618), which is now toggled in the position associated with AUTO-ZERO mode, disconnects the flow path of tube (644) and tube (648) through solenoid valve (618), and connects the flow path of tube (644) and tube (640) through solenoid valve (618). Air, or optionally another gas, may now be drawn into the breath sampling device (600) through intake (621) by the pump (602), the air flowing through the scrubber (610), where $CO_2$ is cleaned from the air. The arrows depict the direction of flow of the breath samples during normal breath sampling operation. Typical flow rates for the air, or optionally another gas, drawn in may be between 10 ml/min and 70 ml/min, for example, 10 ml/min to 20 ml/min, 21 ml/min to 30 ml/min, 31 ml/min to 40 ml/min, 41 ml/min to 50 ml/min, 51 ml/min to 60 ml/min, 61 ml/min to 70 ml/min. The air (without the $CO_2$) flows through tube (640) and through tube (644) to the sensor assembly (608). Calibration of the sensor assembly (608) may now be performed. The air continues to flow in the direction of the pump (602) through tube (646) and subsequently to the exhaust (620) in the breath sampling device (600).

As previously described, when a blockage is detected in the breath sampling tube (614) the pump (602) is deactivated and the solenoid valve (618) toggled from NORMAL mode to AUTO-ZERO mode, allowing air from the ambient to flow back into the breath sampling tube (614). When the solenoid valve (618) is in the AUTO-ZERO mode, air flows into tube (644) and tube (646) between the pump (602) and the solenoid valve (618). When the solenoid valve (618) is toggled to the NORMAL mode, tube (648) and tube (644) are connected so that the air may flow into the breath sampling tube (614), as there is a lower pressure in the breath sampling tube (614). The pump (602) is not operating during this procedure. In applying this method, the solenoid valve (618) is toggled between the NORMAL mode and the AUTO-ZERO mode for a duration between 0.5-10 seconds, for example 2 to 3 seconds, at a frequency ranging from 1 Hz to 50 Hz, for example, at a frequency between the range of 1 Hz to 10 Hz, 11 Hz to 20 Hz, 21 Hz to 35 Hz, 36 Hz to 50 Hz. Toggling for the mentioned duration and frequency is recommended, as the volume of air in tube (644) and (646) from one toggling of the solenoid valve (618) is not sufficient to equalize the pressure in the vacuum in the breath sampling tube (614).

In the description and claims of embodiments of the present invention, each of the words "comprise" "include" and "have", and forms thereof, are not necessarily limited to members in a list with which the words may be associated.

The invention has been described using various detailed descriptions of embodiments thereof that are provided by way of example and are not intended to limit the scope of the invention. The described embodiments may comprise different features, not all of which are required in all embodiments of the invention. Some embodiments of the invention utilize only some of the features or possible combinations of the features. Variations of embodiments of the invention that are described and embodiments of the invention comprising different combinations of features noted in the described embodiments will occur to persons with skill in the art.

What we claim is:

1. A breath sampling device comprising:
   a breath sampling tube;
   a pump configured to create a negative pressure in the breath sampling tube;
   a pressure sensor configured to monitor pressure in said breath sampling tube, wherein pressure reaching a predetermined threshold is indicative of a blockage;
   a valve associated with said breath sampling tube; and
   a controller configured to deactivate said pump when the predetermined pressure threshold is reached and, while said pump is deactivated, to initiate said valve to toggle back and forth between a NORMAL mode of operation, and an AUTO-ZERO mode of operation, said AUTO-ZERO mode of operation allowing air to enter said breath sampling tube between the blockage and the pump, thereby increasing pressure in said breath sampling tube so as to prevent additional liquids from entering said breath sampling tube.

2. The device according to claim 1, wherein the predetermined pressure threshold is a predetermined pressure value within said breath sampling tube.

3. The device according to claim 1, wherein the predetermined pressure threshold is a predetermined pressure change rate within said breath sampling tube.

4. The device according to claim 1, wherein said valve is a solenoid valve.

5. The device according to claim 1, further comprising a restrictor located in proximity to a connection point between an airway adapter and said breath sampling tube, wherein said restrictor is configured to reduce a flow rate of liquids entering said breath sampling tube.

6. The device according to claim 5, wherein said restrictor comprises a restricting hole.

7. The device according to claim 1, further comprising one or more openings located near a connection point between an airway adapter and said breath sampling tube, wherein said one or more openings are configured to allow inflow of air to reduce a flow rate of liquids entering said breath sampling tube.

\* \* \* \* \*